United States Patent [19]

Feyen et al.

[11] 4,218,451

[45] Aug. 19, 1980

[54] PENICILLINS AND THEIR USE

[75] Inventors: Peter Feyen, Mettmann; Hans-Bodo König; Karl G. Metzger, both of Wuppertal, all of Fed. Rep. of Germany

[73] Assignee: Bayer Aktiengesellschaft, Leverkusen, Fed. Rep. of Germany

[21] Appl. No.: 920,505

[22] Filed: Jun. 29, 1978

[30] Foreign Application Priority Data

Jul. 15, 1977 [DE] Fed. Rep. of Germany ....... 2732104

[51] Int. Cl.$^2$ .................. A61K 31/43; A61K 31/495; C07D 499/68

[52] U.S. Cl. ................................ 424/250; 260/239.1; 424/271

[58] Field of Search ..................... 260/239.1; 424/271, 424/250

[56] References Cited

U.S. PATENT DOCUMENTS

| | | | |
|---|---|---|---|
| 3,923,789 | 12/1975 | Schrock et al. | 260/239.1 |
| 3,974,140 | 8/1976 | König et al. | 260/239.1 |
| 3,974,142 | 8/1976 | König et al. | 260/239.1 |
| 3,989,687 | 11/1976 | Bambury et al. | 260/239.1 |
| 3,994,875 | 11/1976 | Patchornik et al. | 260/239.1 |
| 4,031,229 | 6/1977 | König et al. | 424/271 |
| 4,087,424 | 5/1978 | Saikawa et al. | 424/271 |

*Primary Examiner*—Norman Morgenstern
*Assistant Examiner*—Vera C. Clarke
*Attorney, Agent, or Firm*—Sprung, Felfe, Horn, Lynch & Kramer

[57] ABSTRACT

New penicillins of the formula $$X-\overset{\overset{E}{\|}}{C}-NH-\overset{*}{\underset{B}{C}H}-CO-NH-\begin{array}{c}OR_1\\ \end{array}\begin{array}{c}S\\ \diagdown\\ \diagup N\end{array}\begin{array}{c}CH_3\\ CH_3\\ COOH\end{array}$$

in which $$X \text{ is } R_2-N\begin{array}{c}\overset{O}{\|}\\ C\\ \diagdown\\ CH_2-CH_2\end{array}\overset{O}{\underset{\|}{C}}N-,$$

$$R_2-N\begin{array}{c}\overset{O}{\|}\\ C\\ \diagdown\\ CH_2-CH_2\end{array}N-\text{or}$$

$$HN\begin{array}{c}\\ \\ \diagdown\\ O=C\\ \diagdown\\ C\\ |\\ CH_3\end{array}\begin{array}{c}N-\\ \\ CH\end{array}.$$

E is oxygen or sulphur, and
R$_1$ and R$_2$ are hydrogen or various organic radicals with certain provisos, or salts thereof, are antibacterially ative and useful as antibiotics in pharmacy, as animal feed supplements for promoting growth, and as preservatives.

24 Claims, No Drawings

PENICILLINS AND THEIR USE

The present invention relates to certain new penicillin compounds, to processes for their production and to their use as medicaments, in particular as antibacterial agents and as agents for promoting growth and for improving feedstuff utilization in animals.

The penicillin compounds according to the invention have a broad, antibacterial activity. They are active against Gram-negative and Gram-positive germs. The compounds according to the invention further exhibit a high stability towards $\beta$-lactamase and a high activity against those bacteria which form $\beta$-lactamase. Furthermore, the pencillin compounds according to the invention also have the property of protecting other penicillin compounds from destruction by $\beta$-lactamase.

The present invention provides compounds which are penicillins of the following general formula (I) or their salts:

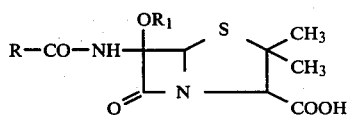

in which
$R_1$ is hydrogen, optionally substituted straight-chain or branched alkyl with preferably 1 to 6, in particular from 1 to 3, carbon atoms, optionally substituted straight-chain or branched alkenyl with preferably from 2 to 6, in particular 3 or 4, carbon atoms, straight-chain or branched alkinyl with the triple bond in the 2-position and with preferably from 3 to 6 carbon atoms, optionally substituted cycloalkyl with preferably from 3 to 9, in particular from 3 to 6 and very preferentially 3 or 4, carbon atoms, optionally substituted aralkyl with preferably from 7 to 10 carbon atoms, optionally substituted aryl with preferably from 6 to 9 carbon atoms or an optionally substituted heterocyclylalkyl or heterocyclic radical which can be, in both cases, 3-membered, 4-membered, 5-membered or 6-membered and can contain oxygen, sulphur and nitrogen, individually or combined or several times individually, as hetero-atoms and can be saturated or unsaturated and R is a radical of the general formula (II) or (IIa)

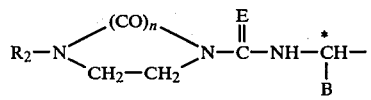

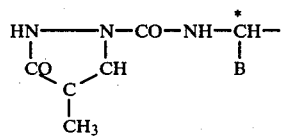

in which
C* is a chirality center which can be in the R-form or S-form,
E is oxygen or sulphur, preferably oxygen,
B is phenyl, substituted phenyl, in particular hydroxyphenyl, preferably p-hydroxyphenyl, cyanophenyl, in particular p-cyanophenyl, methylsulphonylphenyl, in particular p-methylsulphonylphenyl, methylsulphonylaminophenyl, methoxyphenyl or halogenophenyl, in particular fluorophenyl or chlorophenyl, 1-cyclohexen-1-yl or 1,4-cyclohexadien-1-yl,
n denotes 1 or 2 and
$R_2$, in the case where n is 1 and $R_1$ is methyl, is hydrogen, optionally substituted straight-chain or branched alkyl with preferably from 1 to 4, in particular 1 or 2, carbon atoms, optionally substituted straight-chain or branched alkenyl with the double bond in the 2-position, 3-position, 4-position or 5-position and with preferably 3 to 6, in particular 3 or 4, carbon atoms, straight-chain or branched alkinyl with the triple bond in the 2-position, 3-position or 4-position or a radical of the general formula (III) or (IV)

$$R_3\text{—CO—} \quad R_4\text{—SO}_2\text{—}$$
$$\text{(III)} \quad\quad\quad \text{(IV)}$$

in which
$R_3$ is hydrogen or lower alkoxy with preferably 1 to 4, in particular 1 or 2, carbon atoms or
$R_3$ and $R_4$ are the same or different and each is optionally substituted alkyl, optionally substituted alkenyl with the double bond in the 2-position, 3-position, 4-position or 5-position, alkinyl with the triple bond in the 2-position, 3-position or 4-position, amino, lower alkylamino with preferably 1 to 4, in particular 1 or 2, carbon atoms, di-lower alkylamino with preferably from 2 to 6, in particular from 2 to 4, carbon atoms, or an aliphatic heterocyclic ring having a nitrogen atom in the ring via which said $R_3$ or $R_4$ is bonded and optionally one or more further hetero-atoms, such as O, N or S, the heterocyclic ring having preferably from 4 to 6, in particular 5 or 6, ring members, or
$R_3$ and $R_4$ are each optionally substituted cycloalkyl with preferably from 3 to 9, in particular from 3 to 6 and very preferentially 3 or 4, carbon atoms, optionally substituted aralkyl with preferably from 7 to 9 carbon atoms, optionally substituted aryl with preferably from 6 to 8 carbon atoms or an optionally substituted heterocyclic radical which can be 3-membered, 4-membered, 5-membered or 6-membered and can contain oxygen, sulphur and nitrogen, individually or combined or several times individually as hetero-atoms and can be saturated or unsaturated and is, in particular, furane, thiophene, pyrrole, oxazole, isoxazole, thiazole, isothiazole, pyrazole, imidazole, pyridine or pyrimidine, or $R_2$, in the case where n is 2 or $R_1$ is other than methyl, is hydrogen, optionally substituted straight-chain or branched alkyl with preferably from 1 to 6, in particular 1 to 3, carbon atoms, optionally substituted straight-chain or branched alkenyl with preferably from 2 to 6, in particular 3 or 4, carbon atoms, straight-chain or branched alkinyl with the triple bond in the 2-position and with preferably from 3 to 6 carbon atoms, optionally substituted cycloalkyl with preferably from 3 to 9, in particular from 3 to 6 and very preferentially 3 or 4, carbon atoms, optionally substituted aralkyl with preferably from 7 to 10 carbon atoms, optionally substituted aryl with preferably from 6 to 9 carbon atoms or optionally substituted heterocyclylalkyl or heterocyclyl which can be, in both cases, 3-membered, 4-membered, 5-membered or 6-membered and can contain oxygen, sulphur and nitrogen, individually or combined or several times individually, as hetero-atoms and can be saturated or unsaturated.

Among the new salts of the invention, those salts that are pharmaceutically acceptable are particularly important and are preferred.

Salts of the compounds of the formula (I) are salts of these compounds with inorganic and organic bases on the acid carboxyl group or on the acid carboxyl and sulphonic acid groups. Bases which can be used for the pharmaceutically acceptable salts are all the bases customarily used in pharmaceutical chemistry, in particular in the chemistry of antibiotics. Examples of inorganic bases which may be mentioned are: alkali metal hydroxides and alkaline earth metal hydroxides, alkali metal carbonates and alkaline earth metal carbonates and alkali metal bicarbonates, such as sodium hydroxide and potassium hydroxide, calcium hydroxide and magnesium hydroxide, sodium carbonate and potassium carbonate, calcium carbonate and sodium bicarbonate and potassium bicarbonate; and aluminum hydroxide and ammonium hydroxide. Organic bases which can be used are primary, secondary and tertiary aliphatic amines as well as heterocyclic amines. Examples which may be mentioned are: di- and tri-lower alkylamines, for example diethylamine and triethylamine, tri-$\beta$-hydroxyethylamine, procaine, dibenzylamine, N,N'-dibenzylethylenediamine, N-benzyl-$\beta$-phenylethylamine, N-methyl- and N-ethyl-morpholine, 1-ephenamine, dehydroabietylamine, N,N'-bis-dehydroabietylethylenediamine and N-lower alkylpiperidines. So-called basic aminoacids, such as lysine or arginine, can also be advantageously used as bases. Particularly preferred salts are the sodium salts.

Possible substituents for $R_1$, $R_2$, $R_3$ and $R_4$ as an alkyl, alkenyl, cycloalkyl, aryl, aralkyl, heterocyclyl and, optionally, heterocyclylalkyl radical are halogen, preferably fluorine, chlorine and bromine, preferably fluorine and chlorine, lower alkoxy with preferably 1 or 2 carbon atoms, protected hydroxyl, amino or lower alkylamino groups, with preferably 1 or 2 carbon atoms, and carbonyl and sulphonic acid groups, di-lower alkyl-amino groups with preferably from 2 to 4 carbon atoms, keto groups and ester groups with preferably 2 or 3 carbon atoms, carbamyl and sulphamyl radicals, or heterocyclic radicals, such as furanyl, thienyl, pyrrolyl and pyridinyl. Possible substituents for $R_1$, $R_2$, $R_3$ and $R_4$ as heterocyclic radical or heterocyclylalkyl radical are alkyl with preferably 1 or 2 carbon atoms or methyl or ethyl groups which are substituted by a carboxyl or sulphonic acid group.

In a further aspect the present invention provides a process for the production of a compound according to the invention in which a compound of the formula (V)

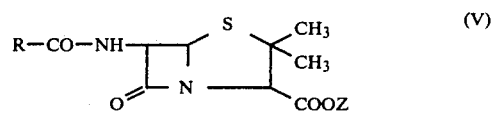

in which
R has the same meaning as defined hereinbefore in formula I, and
Z is hydrogen, acetoxymethyl, an easily removable ester-forming group or the cationic radical of a base, preferably of an alkali metal hydroxide or alkaline earth metal hydroxide, is reacted with preferably from 2 to 10 equivalents, per equivalent of the compound of formula (V) of a base in the presence of an excess of an alcohol of the formula $R_1OH$, in which
$R_1$ has the same meaning as defined in formula I, usually in an inert organic solvent, and preferably from 1 to 8 equivalents, per equivalent of the compound of formula (V), of a N-halogenating agent are added so as to produce a penicillin of the formula (I) as defined hereinbefore or a salt thereof, which is optionally converted into a salt or the corresponding penicillin of formula I, respectively.

The free penicillins of the general formula I and their salts can be interconverted in any suitable manner; methods for such interconversion are known in the art.

In particular, the direct procedure, that is to say the reaction of unprotected compounds of the formula (V), has advantages with respect to the simplicity of carrying out the reaction. In the case where a protective group has been used this will of course be normally removed, conveniently during any customary working-up of the reaction product.

Starting compounds of the formula (V) and of the formula $R_1$—OH are known and can be prepared by known processes.

An example of the process of the invention may be illustrated with the aid of the following reaction equation:

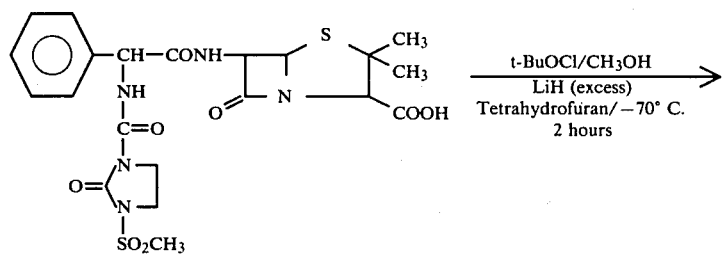

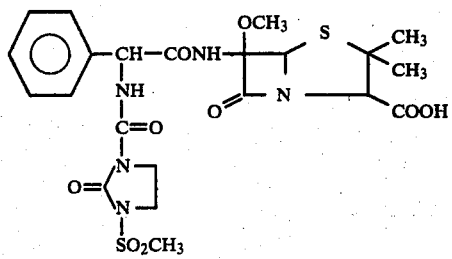

Compounds which transfer positively charged chlorine, such as t-butyl hypochlorite or chloroacetamide, are preferably used as N-halogenating agents in the process according to the invention.

Suitable bases for use in the reaction are complex and simple, but preferably simple, alkali metal hydrides and alkaline earth metal hydrides, metal-organic compounds and Grignard compounds. Examples which may be mentioned are: lithium hydride, sodium hydride, butyl-lithium, phenyl-lithium, alkyl-magnesium bromides, for example methyl-magnesium bromide, or other known acid-binding agents, such as alkali metal alcoholates or carbonates and alkaline earth metal alcoholates or carbonates, alkali metal bicarbonates or oxides and alkaline earth metal bicarbonates or oxides, such as, for example, sodium bicarbonate, or other acid-binding agents, such as sodium tetraborate decahydrate or open-chain or cyclic organic bases, such as trialkylamines or aralkylamines or cyclic amidines, such as 2,3,4,6,7,8-hexahydropyrrolo [1,2-a]pyrimidine (DBN) or 2,3,4,6,7,8,9,10-octahydropyrimido [1,2-a]azepine (DBU). Examples of suitable solvents are openchain or cyclic ethers, aliphatic and aromatic hydrocarbons or halogenohydrocarbons or said alcohol of formula $R_1OH$ itself may serve as a solvent. Tetrahydrofuran is a particularly suitable solvent.

As far as is possible, the reaction temperatures are to be kept below 0° C., preferably at from −100° C. to −45° C. In carrying out a preferred embodiment of the process according to the invention, 1 molar equivalent of the compound of the general formula V is added to the mixture of preferably from 3 to 8 molar equivalents of base, from 2 to more than (if it is itself used as the solvent) 100 molar equivalents of the alcohol $R_1OH$, and the solvent, at a temperature below 0° C., preferably at from −100° C. to −45° C. and from 1 to 5, preferably from 1 to 2, molar equivalents of a halogenating agent (for example t-butyl hypochlorite) are then immediately added. In general, the reaction time is from about 10 minutes to several hours at −70° C. Impurities are then first removed at neutral pH by extraction with an organic solvent. The process product according to the invention is subsequently extracted from the reaction mixture at acid pH. Examples which may be mentioned of compounds according to the invention are:

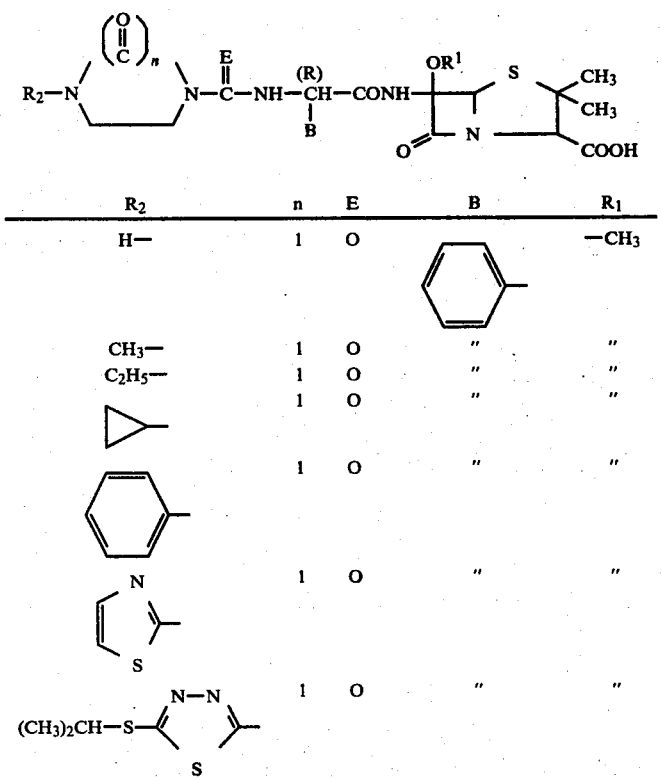

-continued
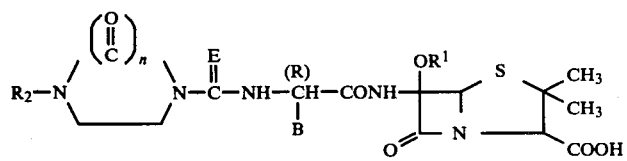
| $R_2$ | n | E | B | $R_1$ |
|---|---|---|---|---|
| | 1 | O | " | " |
| pyrrole-CO— | 1 | O | " | " |
| furan-CO— | 1 | O | " | " |
| $CH_3$—$SO_2$— | 1 | O | " | " |
| thiophene-$SO_2$— | 1 | O | " | " |
| phenyl-$SO_2$— | 1 | O | " | " |
| H— | 1 | O | HO—C$_6$H$_4$— | " |
| $CH_3$— | 1 | O | " | " |
| $C_2H_5$— | 1 | O | " | " |
| cyclopropyl | 1 | O | " | " |
| phenyl | 1 | O | " | " |
| thiazole | 1 | O | " | " |
| $(CH_3)_2$—S—(thiadiazole)— | 1 | O | " | " |
| pyrrole-CO— | 1 | O | " | " |
| furan-CO— | 1 | O | " | " |
| $CH_3$—$SO_2$— | 1 | O | " | " |
| thiophene-$SO_2$— | 1 | O | " | " |
| phenyl-$SO_2$— | 1 | O | " | " |
| H— | 1 | O | thiophene | " |
| $CH_3$— | 1 | O | " | " |
| $C_2H_5$— | 1 | O | " | " |

-continued
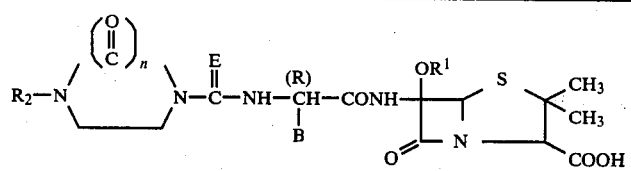
| R$_2$ | n | E | B | R$_1$ |
|---|---|---|---|---|
| cyclopropyl | 1 | O | " | " |
| phenyl | 1 | O | " | " |
| thiazolyl | 1 | O | " | " |
| (CH$_3$)$_2$-S- (thiadiazolyl) | 1 | O | " | " |
| pyrrolyl-CO- | 1 | O | " | " |
| furyl-CO- | 1 | O | " | " |
| CH$_3$-SO$_2$- | 1 | O | " | " |
| thienyl-SO$_2$- | 1 | O | " | " |
| phenyl-SO$_2$- | 1 | O | " | " |
| H- | 1 | O | cyclohexadienyl | " |
| CH$_3$- | 1 | O | " | " |
| C$_2$H$_5$- | 1 | O | " | " |
| cyclopropyl | 1 | O | " | " |
| phenyl | 1 | O | phenyl | " |
| thiazolyl | 1 | O | " | " |
| (CH$_3$)$_2$CH-S- (thiadiazolyl) | 1 | O | " | " |
| pyrrolyl-CO- | 1 | O | " | " |
| furyl-CO- | 1 | O | " | " |

-continued
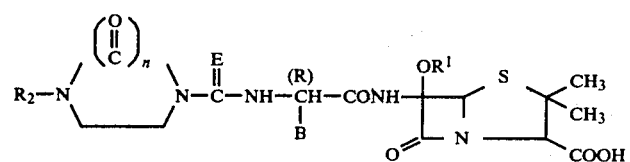
| R₂ | n | E | B | R₁ |
|---|---|---|---|---|
| CH₃—SO₂— | 1 | O | " | " |
| thiophene-SO₂— | 1 | O | " | " |
| phenyl-SO₂— | 1 | O | " | " |
| H— | 2 | O | " | " |
| CH₃— | 2 | O | " | " |
| C₂H₅— | 2 | O | " | " |
| cyclopropyl | 2 | O | " | " |
| phenyl | 2 | O | " | " |
| thiazolyl | 2 | O | " | " |
| (CH₃)₂CH—S—(thiadiazolyl) | 2 | O | " | " |
| pyrrole-CO— | 2 | O | " | " |
| furan-CO— | 2 | O | " | " |
| CH₃—SO₂— | 2 | O | " | " |
| thiophene-SO₂— | 2 | O | " | " |
| phenyl-SO₂— | 2 | O | " | " |
| H— | 2 | O | HO—C₆H₄— | " |
| CH₃— | 2 | O | " | " |
| C₂H₅— | 2 | O | " | " |
| cyclopropyl | 2 | O | " | " |
| phenyl | 2 | O | " | " |
| thiazolyl | 2 | O | " | " |

-continued
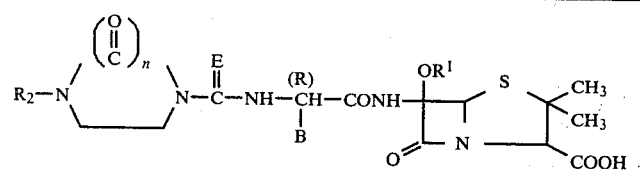
| R₂ | n | E | B | R₁ |
|---|---|---|---|---|
| (CH₃)₂CH-S-[thiadiazole-CH₃] | 2 | O | " | " |
| [pyrrole]-CO- | 2 | O | " | " |
| [furan]-CO- | 2 | O | " | " |
| CH₃-SO₂- | 2 | O | " | " |
| [thiophene]-SO₂- | 2 | O | " | " |
| [phenyl]-SO₂- | 2 | O | " | " |
| H | 2 | O | [thiophene] | " |
| CH₃- | 2 | O | " | " |
| C₂H₅- | 2 | O | " | " |
| [cyclopropyl] | 2 | O | " | " |
| [phenyl] | 2 | O | " | " |
| [thiazole] | 2 | O | " | " |
| CH₃CH-S-[thiadiazole-CH₃] | 2 | O | " | " |
| [pyrrole]-CO- | 2 | O | " | " |
| [furan]-CO- | 2 | O | " | " |
| CH₃-SO₂- | 2 | O | " | " |
| [thiophene]-SO₂ | 2 | O | " | " |
| [phenyl]-SO₂- | 2 | O | " | " |

-continued
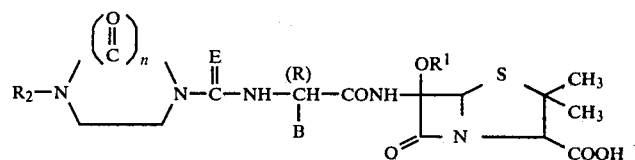
| R₂ | n | E | B | R₁ |
|---|---|---|---|---|
| H— | 2 | O | (cyclohexadienyl) | " |
| CH₃— | 2 | O | " | " |
| C₂H₅— | 2 | O | " | " |
| cyclopropyl | 2 | O | " | " |
| phenyl | 2 | O | " | " |
| thiazol-2-yl | 2 | O | " | " |
| (CH₃)₂CH—S—(thiadiazolyl) | 2 | O | " | " |
| pyrrol-2-yl-CO— | 2 | O | " | " |
| furan-2-yl-CO— | 2 | O | " | " |
| CH₃—SO₂— | 2 | O | " | " |
| thienyl-SO₂— | 2 | O | " | " |
| phenyl-SO₂— | 2 | O | " | " |
| H | 1 | O | (cyclohexadienyl) | —C₂H₅ |
| CH₃— | 1 | O | " | " |
| C₂H₅ | 1 | O | " | " |
| cyclopropyl | 1 | O | " | " |
| phenyl | 1 | O | " | " |
| thiazol-2-yl | 1 | O | " | " |
| (CH₃)₂CH—S—(thiadiazolyl) | 1 | O | " | " |

-continued
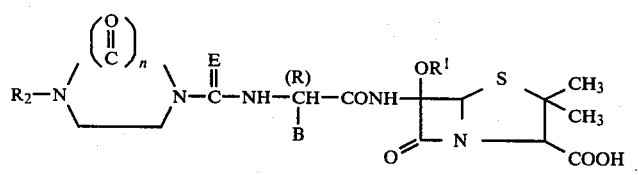
| $R_2$ | n | E | B | $R_1$ |
|---|---|---|---|---|
|  | 1 | O | " | " |
| ⌬(NH)—CO— (pyrrole-2-CO) | 1 | O | " | " |
| ⌬(O)—CO— (furan-2-CO) | 1 | O | " | " |
| $CH_3-SO_2-$ | 1 | O | " | " |
| ⌬(S)—SO₂— (thiophene-SO₂) | 1 | O | " | " |
| C₆H₅—SO₂— | 1 | O | " | " |
| H— | 1 | O | HO—C₆H₄— | " |
| $CH_3-$ | 1 | O | " | " |
| $C_2H_5-$ | 1 | O | " | " |
| cyclopropyl | 1 | O | " | " |
| C₆H₅— | 1 | O | " | " |
| thiazol-2-yl | 1 | O | " | " |
| $(CH_3)_2CH-S-$(5-methyl-1,3,4-thiadiazol-2-yl-S-) | 1 | O | " | " |
| pyrrole-2-CO— | 1 | O | " | " |
| furan-2-CO— | 1 | O | " | " |
| $CH_3-SO_2-$ | 1 | O | " | " |
| thiophene-SO₂— | 1 | O | " | " |
| C₆H₅—SO— | 1 | O | " | " |
| H— | 1 | O | thiophene | " |
| $CH_3-$ | 1 | O | " | " |
| $C_2H_5-$ | 1 | O | " | " |

-continued
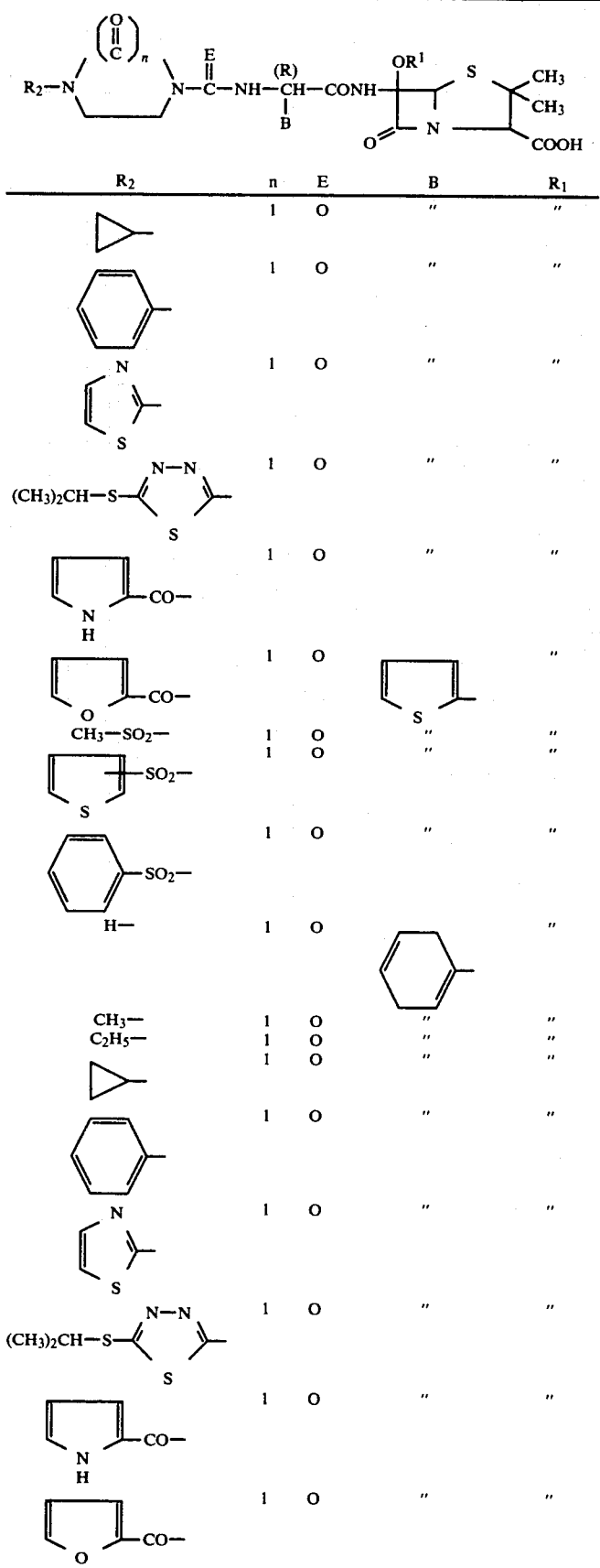
| R₂ | n | E | B | R₁ |
|---|---|---|---|---|
| cyclopropyl | 1 | O | " | " |
| phenyl | 1 | O | " | " |
| thiazolyl (N,S) | 1 | O | " | " |
| (CH₃)₂CH—S— thiadiazolyl | 1 | O | " | " |
| pyrrolyl-CO— (NH) | 1 | O | " | " |
| furyl-CO— | 1 | O | thienyl | " |
| CH₃—SO₂— | 1 | O | " | " |
| thienyl-SO₂— | 1 | O | " | " |
| phenyl-SO₂— | 1 | O | " | " |
| H— | 1 | O | cyclohexadienyl | " |
| CH₃— | 1 | O | " | " |
| C₂H₅— | 1 | O | " | " |
| cyclopropyl | 1 | O | " | " |
| phenyl | 1 | O | " | " |
| thiazolyl | 1 | O | " | " |
| (CH₃)₂CH—S— thiadiazolyl | 1 | O | " | " |
| pyrrolyl-CO— (NH) | 1 | O | " | " |
| furyl-CO— | 1 | O | " | " |

-continued
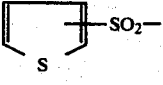
| R₂ | n | E | B | R₁ |
|---|---|---|---|---|
| CH₃—SO₂— | 1 | O | " | " |
| 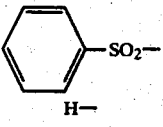 | 1 | O | " | " |
| 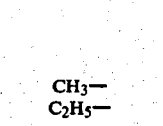 | 1 | O | " | " |
| H— | 2 | O | 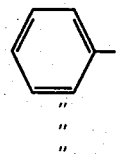 | " |
| CH₃— | 2 | O | " | " |
| C₂H₅— | 2 | O | " | " |
|  | 2 | O | " | " |
|  | 2 | O | " | " |
| 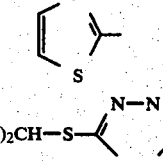 | 2 | O | " | " |
| (CH₃)₂CH—S—  | 2 | O | " | " |
| 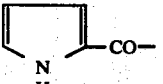 | 2 | O | " | " |
| 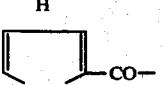 CH₃—SO₂ | 2 | O | " | " |
| 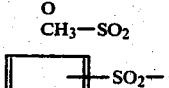 | 2 | O | " | " |
| 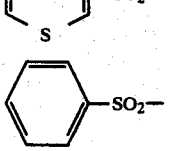 | 2 | O | " | " |
| H— | 2 | O | " | " |
| CH₃— | 2 | O | " | " |
| C₂H₅— | 2 | O | " | " |
|  | 2 | O | " | " |
| 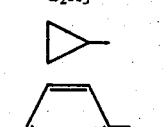 | 2 | O | " | " |
| 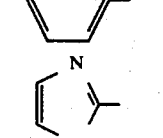 | 2 | O | " | " |

-continued
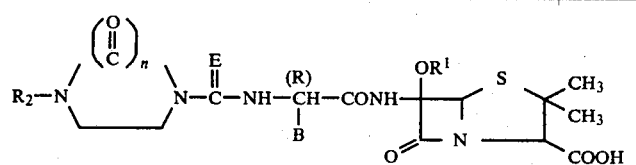
| R₂ | n | E | B | R₁ |
|---|---|---|---|---|
| (CH₃)₂CH—S—[thiadiazole]—S— | 2 | O | " | " |
| [pyrrole]—CO— | 2 | O | " | " |
| [furan]—CO— | 2 | O | " | " |
| CH₃—SO₂— | 2 | O | " | " |
| [thiophene]—SO₂— | 2 | O | " | " |
| [phenyl]—SO₂— | 2 | O | " | " |
| H— | 2 | O | [thiophene] | " |
| CH₃— | 2 | O | " | " |
| C₂H₅— | 2 | O | " | " |
| [cyclopropyl] | 2 | O | " | " |
| [phenyl] | 2 | O | " | " |
| [thiazoline] | 2 | O | " | " |
| (CH₃)₂—S—[thiadiazole]—S— | 2 | O | " | " |
| [pyrrole]—CO— | 2 | O | " | " |
| [furan]—CO— | 2 | O | " | " |
| CH₃—SO₂— | 2 | O | " | " |
| [thiophene]—SO₂— | 2 | O | " | " |
| [phenyl]—SO₂— | 2 | O | " | " |
| H— | 2 | O | " | " |
| CH₃— | 2 | O | " | " |
| C₂H₅— | 2 | O | " | " |

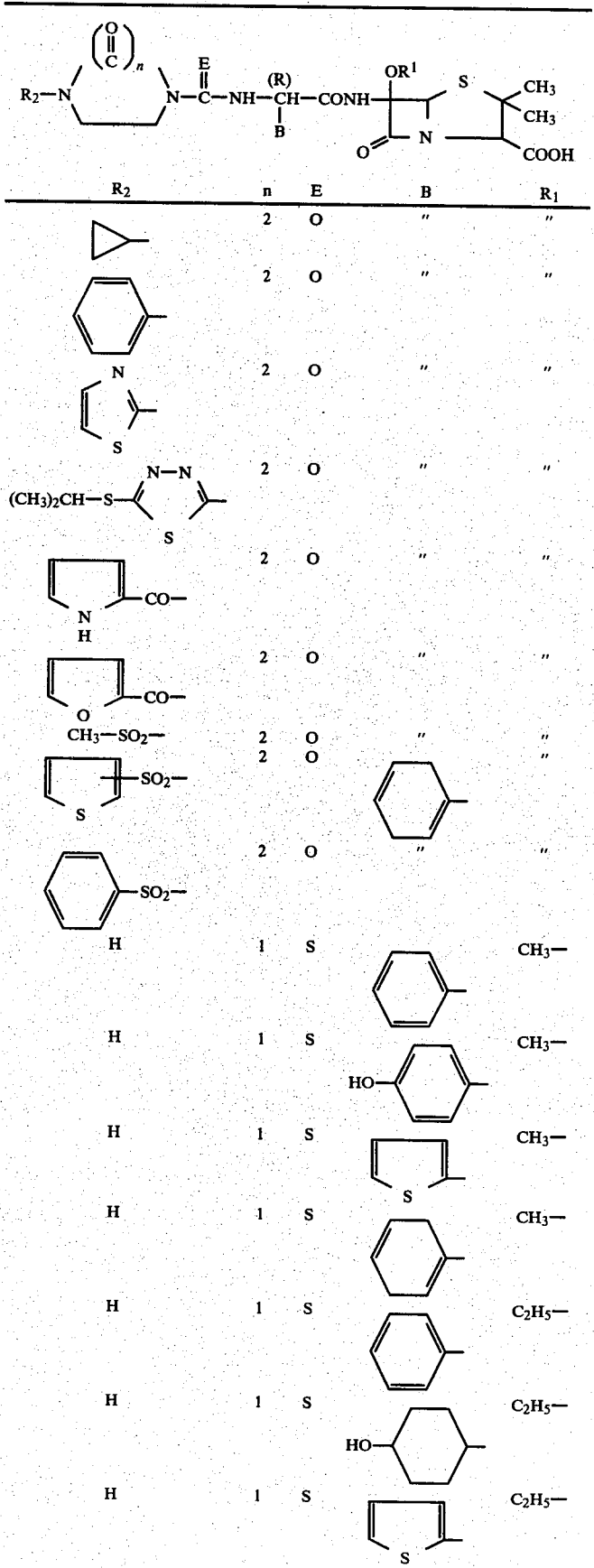

-continued

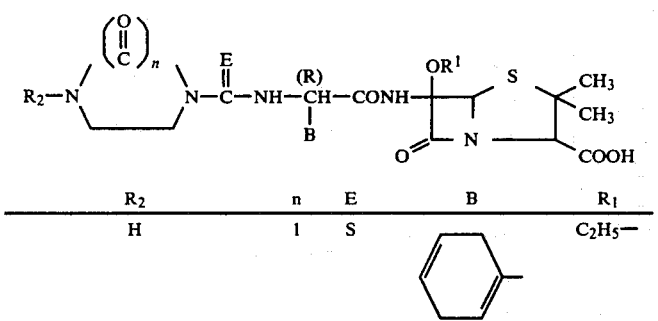

| R₂ | n | E | B | R₁ |
|---|---|---|---|---|
| H | 1 | S | [cyclohexenyl] | C₂H₅— |

The active compounds according to the invention display a powerful antimicrobial activity. These properties enable them to be used as active compounds in medicine and as substances for preserving inorganic and organic materials, especially organic materials of all kinds, for example polymers, lubricants, paints, fibers leather, paper and timber, foodstuffs and water.

The active compounds according to the invention are active against a very broad spectrum of micro-organisms. With their aid it is possible to combat, for example, Gram-negative and Gram-positive bacteria and bacteria-like microorganisms, and to prevent, alleviate and/or cure diseases caused by these pathogens.

The active compounds according to the invention are particularly active against bacteria and bacteria-like microorganisms. They are therefore particularly suitable for the prophylaxis and chemotherapy in human medicine and veterinary medicine of local and systemic infections caused by these pathogens.

For example, local and/or systemic diseases which are caused by the following pathogens or by mixtures of the following pathogens can be treated and/or prevented:

Microoccoccaceae, such as Staphylococci, for example *Staphylococcus aureus, Staph. epidermidis* and *Staph. aerogenes* (Staph=Staphylococcus);

Lactobacteriaceae, such as Streptococci, for example *Streptococcus pyogenes*, α- and β-haemolysing Streptococci, non (γ-)-haemolysing Streptococci, *Str. viridans, Str. faecalis* (Enterococci), *Str.agalactiae, Str. Lactis, Str. equi, Str. anaerobis* and *Diplococcus pneumoniae* (Pneumococci) (Str.=Streptococcus);

Neisseriaceae, such as Neisseriae, for example *Neisseria gonorrhoeae* (Gonoccoci), *N. meningitidis* (Meningococci), *N. catarrhalis* and *N. flava* (N.=Neisseria);

Corynebacteriaceae, such as Corynebacteria, for example *Corynebacterium diphtheriae, C. pyogenes, C. diphtheroides, C. acnes, C. parvum, C. bovis, C. renale* and *C. ovis,*

Enterobacteriaceae, such as Escherichiae bacteria of the Coli group, Escherichia bacteria, for example *Escherichia coli,* Enterobacter bacteria, for example *E. aerogenes* and *E. cloacae,* Klebsiella bacteria, for example *K. pneumoniae,* Serratia, for example *Serratia marcescens* (E.=Enterobacter) (K.=Klebsiella), Proteae bacteria of the Proteus group, Proteus, for example *Proteus vulgaris, Pr. morganii, Pr. rettgeri* and *Pr. mirabilis* (Pr.=Proteus), Providencia, for example Providencia sp., Salmonelleae, Salmonella bacteria, for example *Salmonella paratyphi A* and *B, S. typhi, S. enteritidis, S. cholerae suis* and *S. typhimurium* (S.=Salmonella), and Shigella bacteria, for example *Shigella dysenteriae;*

Pseudomonadaceae, such as Pseudomonas bacteria, for example *Pseudomonas aeruginose* and *Ps. pseudomallei* (Ps.=Pseudomonas), and Aeromonas bacteria, for example *Aeromonas liquefaciens* and *A. hydrophila* (A.-=Aeromonas);

Spirillaceae, such as Vibrio bacteria, for example *Vibrio cholerae* and *V. proteus* (V.=Vibrio);

Parvobacteriaceae or Brucellaceae, such as Pasteurella bacteria, for example *Pasteurella multocida, Past. pestis* (Yersinia) and *Past. pseudotuberculosis* (Past.=Pasteurella), Haemophilus bacteria, for example *Haemophilus influenzae,* and Bordetella bacteria, for example *B. bronchiseptica* (B.=Bordetella);

Bacteroidacea, such as Bacteroides bacteria, for example *Bacteroides fragilis* and *B. serpens* (B.=Bacteroides), Fusiforme bacteria, for example *Fusobacterium fusiforme,* and Sphaerophorus bacteria, for example *Sphaerophorus necrophorus, Sph. necroticus* and *Sph.pyrogenes* (Sph.=Sphaerophorus);

Bacillaceae, such as aerobic spore-forming Bacillaceae, for example *Bacillus anthracis, B. subtilis* and *B. cereus* (B.=Bacillus), anaerobic spore-forming Clostridia, for example *Clostridium perfringens, Cl. tetani* and *Cl. botulinum* (Cl.=Clostridium);

The above list of pathogens is purely illustrative and is in no way to be interpreted as restrictive.

Examples which may be mentioned of diseases which can be prevented, alleviated and/or cured by the active compounds according to the invention are: diseases of the respiratory passages and of the pharyngeal cavity; otitis; pharyngitis; pneumonia; peritonitis; pyelonephritis; cystitis; endocarditis; systemic infections; bronchitis; and arthritis.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:
(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quanternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-actice agents (e.g. ethoxylated isostearyl alcohols, polyoxyethylene sorbite and sorbitan esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for administration of the medicaments of the invention is from 300 mg to 40 g, preferably from 750 mg to 15 g of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously or intravenously), rectally or locally, preferably parenterally, especially intravenously and intramuscularly. Preferred pharmaceutical compositions and medicaments are therefore those adapted for parenteral administration, such as injection solutions and suspensions and ampules thereof. Administration in the method of the invention is preferably parenteral.

In general it has proved advantageous to administer amounts of from 6 mg to 800 mg, preferably from 15 mg to 300 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, while in other cases the upper limit mentioned must be exceeded to achieve the desired results. Where larger amounts are administered it can be advisable to divide these into several, for example 3, individual administrations over the course of the day. An individual administration preferably contains from 2 to 300, most preferably, from 10 to 150 mg of active compound per kg of body weight.

When used as feedstuff additives, the new compounds can be administered in the customary manner together with the feedstuff or with feedstuff formulations or with the drinking water. By this means it is possible to prevent an infection by Gram-negative or Gram-positive bacteria and also to achieve better utilization of the feedstuff and promotion of growth. The invention accordingly also relates to an animal feedstuff that contains the new penicillins in the presence of carriers or additives which can be used for animal nutrition, and to a process for the preparation of such a feedstuff.

The new penicillins are distinguished by powerful antibacterial actions, which have been tested in vivo and in vitro, and by oral resorbability.

In order to broaden the spectrum of action or to achieve a more powerful action, the penicillins according to the invention can also be combined with, for example, aminoglycoside antibiotics, such as gentamycin, sisomycin, kanamycin, amicacin or tobramycin.

The activity of the penicillins according to the invention can be demonstrated, by way of example, by the following in vitro and in vivo experiments:

1. In vitro experiments

The compounds of the following Examples 2, 5 and 8, which can be regarded as typical representatives of the compounds according to the invention, were diluted to a concentration of 100 μg/ml with Müller-Hinton nutrient broth. In each case, the nutrient solution contained $1 \times 10^5$ to $2 \times 10^5$ bacteria per milliliter. The small tubes containing this batch were in each case incubated for 24 hours and the degree of turbidity was then determined. Freedom from turbidity indicates activity. At a dosage of 100 μg/ml, the following bacterial cultures were free from turbidity (sp.=species):

Klebsiella pneumoniae; Enterobacter aerogenes sp.; Providencia; Serratia marcescens; E. coli BE; Salmonella sp.; Shigella sp.; Proteus, indole negative and indole - positive; Pasteurella pseudotuberculosis; Haemophilus influenzae; Bordetella bronchiseptica; Staphylococcus aureus 133; Neisseria catarrhalis sp.; Diplococcus pneumoniae sp.; Streptococcus pyogenes W.; Enterococcuc sp.; Lactobacillus sp.; Corynebacterium diphteriae gravis; Corynebacterium pyogenes M; Clostridium tetani; and Pseudomonas aeruginosa sp..

2. In vivo experiments

Table 1 which follows shows the action of one of the compounds according to the invention against a number of bacteria in an animal experiment using white mice. White mice of the $CF_1$ strain were infected intraperitoneally with the particular species of bacteria indicated.

TABLE 1

Animal experiments using white mice

Determination of the $ED_{100}$ after 24 hours

| Germ | Dose in mg of the compounds of Examples 1,2 and 9 per kg body weight (subcutaneously) |
|---|---|
| Escherichia coli C 165 | 2 × 150 |
| Klebsiella 63 | 2 × 150 |

Therapy: two administrations: 30 minutes and 90 minutes after infection. The $ED_{100}$ is the dose at which 100% of the infected animals still survive after 24 hours.

EXAMPLE 1

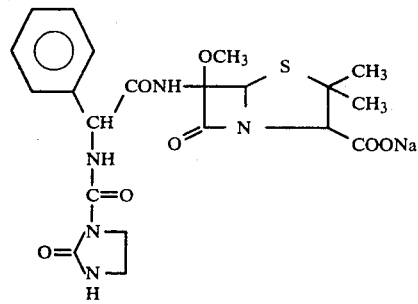

150 parts by volume of tetrahydrofuran and 0.57 parts by weight of lithium hydride, dissolved in 100 parts by volume of methanol, are initially introduced at −70° C. under nitrogen and 8.3 parts by weight of D-α-(imidazolidin-2-on-1-yl-carbonyl-amino)-benzylpenicillin are added. Finally, 5.9 parts by weight of t-butyl hypochlorite are then also added directly thereafter. The mixture is then further stirred at −60° C. for 4 hours.

Working up is carried out by introducing the reaction solution into 200 parts by volume of water, while simultaneously adding dilute hydrochloric acid so that the pH value remains at about 7.5.

After extracting organic impurities with ethyl acetate, rendering the mixture acid (pH 1.8) and extracting the product with ethyl acetate, the latter ethyl acetate phases are covered with a layer of water, and dilute sodium hydroxide solution is slowly added while cooling, until a pH value of 6.5-7.5 is obtained.

This aqueous phase is freeze-dried. This gives 7.2 g (78%) of 6-α-methoxy-6-β-[D-2-(imidazolidin-2-on-1-yl-carbonylamino)-phenylacetamido]-penicillanic acid (sodium salt).

The thin layer chromatogram shows a virtually pure compound. (The running agent system used was: 200 ml of n-butyl acetate/36 ml of n-butanol/100 ml of acetic acid, shaken with 60 ml of phosphate buffer pH 7, (1/15) M. The organic phase was used.)

The IR spectrum contains the necessary β-lactam band at 1,760 cm$^{-1}$. 100 MHz $^1$H—NMR spectrum (acetone/D$_2$O) (shift values δ, TMS as the internal standard): 0.8 s 3H, 1.1 s 3H, 3.1–3.3 m 2H, 3.3 s 3H, 3.5–3.65 m 2H (somewhat overlaid by the H$_2$O signal), 3.85 s 1H, 5.3 s 1H, 5.4 s 1H and 7.2 m 5H.

EXAMPLE 2

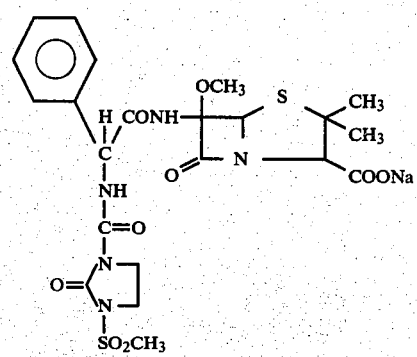

The procedure is analogous to Example 1.

The following compounds were employed: 22.5 parts by weight of D-α-[3-(methylsulphonyl)-imidazolidin-2-on-1-yl-carbonylamino]-benzylpenicillin, 1.27 parts by weight of lithium hydride, 4.34 parts by weight of t-butyl hydrochlorite, 500 parts by volume of tetrahydrofuran and 500 parts by volume of methanol.

Reaction time 2 hours at −60° C.

Yield: 20.1 parts by weight (85%) of 6-α-methoxy-6-β-[D-2-[(3-methylsulphonyl)-imidazolidin-2-on-1-yl-carbonylamino]-phenylacetamido]-penicillanic acid (sodium salt)

Thin layer chromatogram: single compound, IR spectrum: β-lactam band at 1.760 cm$^{-1}$ NMR spectrum (D$_2$O) 1.2 s 3H, 1.6 s 3H, 3.6 s 3H, 3.8 s 3H, 4.1 m 4H, 4.4 s 1H, 5.7 s 1H, 5.8 s 1H and 7.2 broad s 5H.

EXAMPLE 3

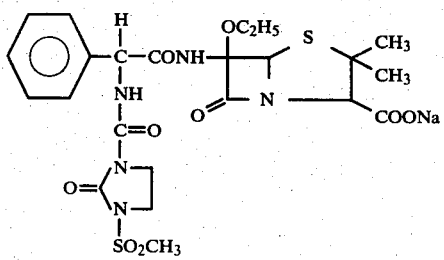

The procedure is analogous to Example 1.

Compounds employed: 8.1 parts by weight of D-α-[3-(methylsulphonyl)-imidazolidin-2-on-1-yl-carbonylamino]-benzylpenicillin, 0.48 part by weight of lithium hydride, 32 parts by weight of t-butyl hydrochlorite, 80 parts by volume of tetrahydrofuran and 100 parts by volume of methanol.

Reaction time 2 hours at −60° C.

Yield: 7.5 parts by weight (82%) of 6-α-ethoxy-6-β-[D-2-β-[(3-methylsulphonyl)-imidazolidin-2-on-1-yl-carbonylamino]-phenylacetamido]-penicillanic acid (sodium salt).

Thin layer chromatogram: the compound still contains some starting material but is otherwise pure (about 90% pure) and has a significantly higher R$_f$ value than the starting compound.

IR: 1,760 cm$^{-1}$

NMR: 1.0 s 3H, 1.2 s 3H, 1.3 s double t 3H, 3.3 s 3H, m 2H overlaid by this, 3.8 m 4H, 4.05 s 1H, 5.45 s 1H, 5.5 s 1H and 7.4 m 5H.

EXAMPLE 4

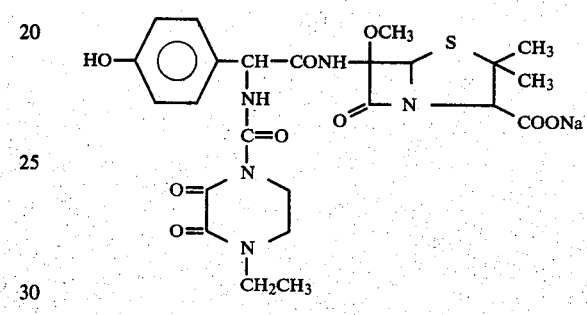

For the experimental procedure see Example 1.

Compounds employed: 3 parts by weight of 6[D-α-(4-ethyl-2,3-dioxo-1-piperazino-carbonylamino)-p-hydroxyphenylacetamido]-penicillanic acid, 1.3 parts by volume of t-butyl hypochlorite, 120 parts by volume of tetrahydrofuran 120 parts by volume of CH$_3$OH and 0.22 part by weight of LiH.

Reaction time 3 hours at −60° C. to −70° C.

Yield 2.3 parts by weight (75% of 6-α-methoxy-6-β-[D-2-(4-ethyl-2,3-dioxopiperazinocarbonylamino)-p-hydroxyphenylacetamido]-penicillanic acid (sodium salt)

IR spectrum (Nujol): 1,750 cm$^{-2}$

NMR spectrum (d-acetone/D$_2$O): 4.1 s 1H (somewhat overlaid by the solvent), 5.6 broad s 1H+1H and 7.0–7.6 m 4H.

EXAMPLE 5

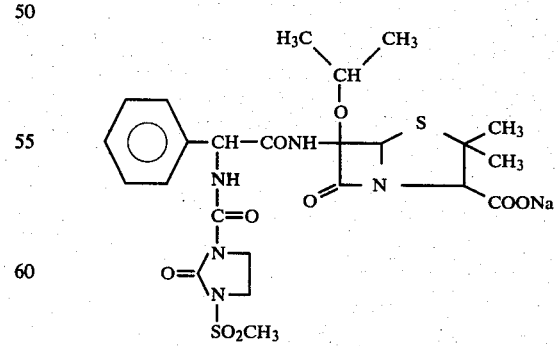

Experimental procedure as in Example 1.

Compounds employed: 10.8 parts by weight of D-α-[3-(methylsulphonyl)-imidazolin-2-on-1-yl-carbonylamino]-benzylpenicillin, 100 parts by volume of tetrahydrofuran 48.75 parts by volume of a 15% strength solution of n-butyl-lithium in n-hexane, 100 parts by volume of i-propanol and 2.17 parts by weight of t-butyl hypochlorite.

The alcoholate solution is appropriately prepared separately before-hand from butyl-lithium and i-propanol and then added to the cooled tetrahydrofuran solution.

Reaction time 4.5 hours at −60° C.

Yield: 8.8 parts by weight (71%) of 6-α-isopropoxy-6-β-[D-2-[3-methylsulphonyl)imidazolidin-2-on-1-yl-carbonylamino]phenylacetamido]-penicillanic acid (sodium salt)

IR spectrum: shoulder at 1,760 cm$^{-1}$ (Nujol)

NMR spectrum: 0.95 s 3H, 1.1–1.25 double doublet 3H, 1.33 s 3H, 1.55 d 3H, 3=4 Hz, 3.35 s 3H, septet overlaid by this 1H, 3.9 broad s 4H, 4.00 s 1H (last two signals partially overlaid by the solvent) 5.49 s 1H, 5.5 s 1H and 7.2–7.6 m 5H

EXAMPLE 6

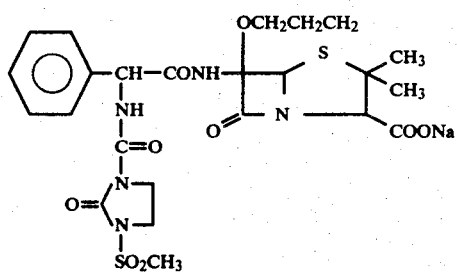

The procedure is as in Example 1.

Compounds employed: 8.1 parts by weight of D-α-[3-methylsulphonyl)-imidazolidin-2-on-1-yl-carbonylamino]-benzyl-penicillin, 36 parts by volume of a 15% strength solution of n-butyl-lithium in n-hexane, 100 parts by volume of tetrahydrofuran 100 parts by volume of n-propane and 3.2 parts by weight of t-butyl hypochlorite.

The alcoholate solution is again prepared beforehand (see Example 5).

Reaction time 2 hours at −60° to −70° C.

Yield: 5.5 parts by weight (60%) of 6-α-(1-propoxy)-6-β-[D-2-[3-(methylsulphonyl)-imidazolidin-2-on-1-yl-carbonylamino]-phenylacetamido]-penicillanic acid (sodium salt)

EXAMPLE 7

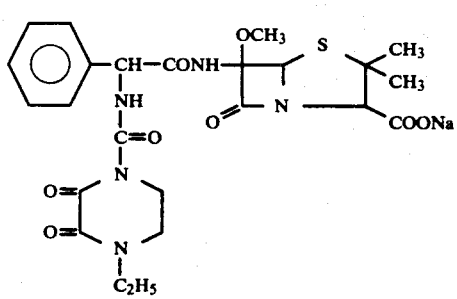

The reaction was carried out as described in Example 1.

Compounds employed: 2.2 parts by weight of 6[D-α-(4-ethyl-2,3-dioxo-1-piperazino-carbonylamino)-phenylacetamido]-penicillanic acid, 0.48 part by volume of t-butyl hypochlorite, 100 parts by volume of tetrahydrofuran 100 parts by volume of CH₃OH and 0.13 part by weight of lithium hydride.

Reaction time 3 hours at −70° C.

The compound was precipitated as the sodium salt by introducing the concentrated ethyl acetate solution (after the acid extraction) into an ethereal/methanolic solution of sodium 2-ethylhexanoate, which contained ⅔ of the theoretical amount of sodium 2-ethylhexanoate, while stirring vigorously.

The precipitate was filtered off and, after 20 minutes, was stirred in 10% CH₃OH/ether. After filtering off again, 1.3 parts by weight of 6-α-methoxy-6-[D-2-(4-ethyl-2,3-dioxo-1-piperazinocarbonylamino)-phenylacetamido]-penicillanic acid (sodium salt) were obtained.

EXAMPLE 8

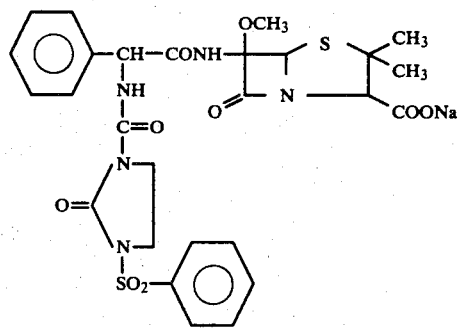

For the procedure, see Example 1.

Compounds employed: 9 parts by weight of D-α-[3-(phenylsulphonyl)-imidazolidin-2-on-1-yl-carbonylamino]-benzylpenicillin. 0.48 part by weight of lithium hydride, 1.6 parts by weight of t-butyl hypochlorite, 100 parts by volume of CH₃OH and 100 parts by volume of tetrahydrofuran.

Yield: 7.2 parts by weight (73.5%) of 6-α-methoxy-6-β-[D-2-[3-(phenylsulphonyl)-imidazolidin-2-on-1-yl-carbonylamino]-phenylacetamido]-penicillanic acid Thin layer chromatogram: single compound, IR spectrum (Nujol), β-lactam band at 1,760 cm$^{-1}$ NMR spectrum (d-acetone/D₂O) 1.0 s 3H, 1.3 s 2H, 3.4 s 3H, 3.9 m 4H, 4.0 s 1H, 5.4 s 1H, 5.5 s 1H and 7.2–5.0 m 10H.

EXAMPLE 9

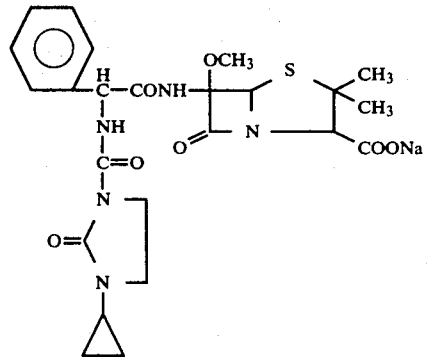

The procedure is as in Example 1.

Compounds employed: 2.5 parts by weight of D-α-[3-(cyclopropyl)-imidazolidin-2-on-1-yl-carbonylamino]-benzylpenicillin, 0.16 part by weight of LiH, 0.54 part by weight of butyl hypochlorite, 50 parts by volume of tetrahydrofuran and 50 parts by volume of CH₃OH.

Reaction time 3 hours at −60° to −70° C.

Yield: 1.9 parts by weight (68%) of 6-α-methoxy-6-β-[D-2-(3-cyclopropyl-imidazolidin-2-on-1-yl-carbonylamino)-phenylacetamido]-penicillanic acid (sodium salt)

Thin layer chromatogram: single compound, IR (Nujol): 1,760 cm⁻¹

NMR spectrum (CD₃OD): 0.75 d 4H, 0.9 s 3H, 1.3 s 3H, 2.45 p 1H, 3.3 m 2H, 3.45 s 3H, 3.65 m 2H, 4.05 s 1H, 5.4 s 1H, 5.5 s 1H and approximately 7.3 m 5H.

EXAMPLE 10

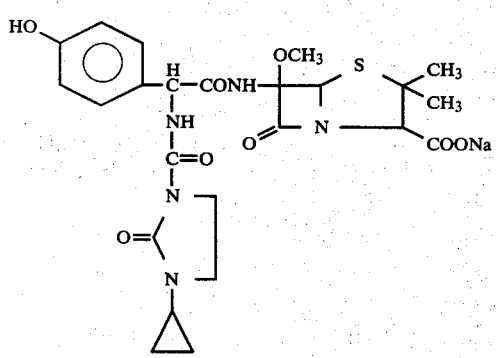

For the experimental procedure see Example 1.

Compounds employed: 1.92 parts by weight of 6[D-α-(3-cyclopropyl-imidazolidin-2-on-1-yl-carbonylamino)-p-hydroxyphenyl-acetamido]-penicillanic acid, 0.15 part by weight of lithium hydride, 0.8 part by weight of t-butyl hypochlorite, 50 parts by volume of tetrahydrofuran and 50 parts by volume of CH₃OH Reaction time 3.5 hours at −65° C.

Yield: 1.5 parts by weight (71%) of 6-α-methoxy-6-β-[D-2-(3-cyclopropyl-imidazolidin-2-on-1-yl-carbonylamino)-p-hydroxy-phenyl-acetamido]-penicillanic acid (sodium salt)

Thin layer chromatogram: single compound; IR (Nujol): 1,760 cm⁻¹

NMR (CD₃OD): 0.73 d 4H, 1.0 s 3H, 1.35 s 3H, 3.5 p 1H, 3.35 m 2H, 3.45 s 3H, 3.7 m 2H, 4.1 s 1H, 5.4 s 1H, 5.5 s 1H, 6.8 m 2H and 7.35 m 2H.

EXAMPLE 11

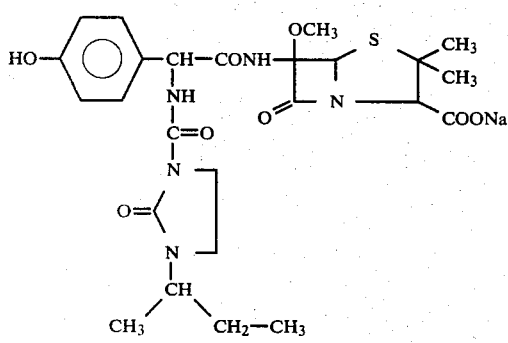

The procedure is as described in Example 1.

Yield: 68% of 6-α-methoxy-6-β-{D-2-[3-(1-methylpropyl-)imidazolidin-2-on-1-yl-carbonylamino]-p-hydroxyphenylacetamido}-penicillanic acid (sodium salt)

Thin layer chromatogram: single compound, IR (Nujol): 1,760 cm⁻¹

NMR spectrum (CD₃OD): 0.85 t 3H, 1.1 m 6H, 1.5 m 5H, 3.4 m 2H, 3.5 s 3H, 3.7 m 2H, 4.1 s 1H, 5.4 s 1H, 5.5 s 1H, 6.8 m 2H and 7.3 m 2H.

EXAMPLE 12

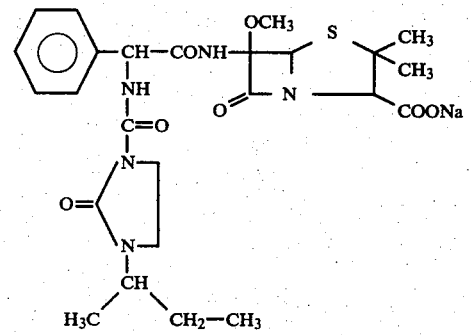

The procedure is as described in Example 1.

Yield: 64% of 6-α-methoxy-6-β-{D-2-[3-(1-methylpropyl)-imidazolidin-2-on-1-yl-carbonylamino]-phenylacetamido}-penicillanic acid (sodium salt)

IR spectrum (Nujol): band at 1,785 cm⁻¹

Except for the changed aromatic proton signals, the NMR spectrum corresponds to that from Example 11.

EXAMPLE 13

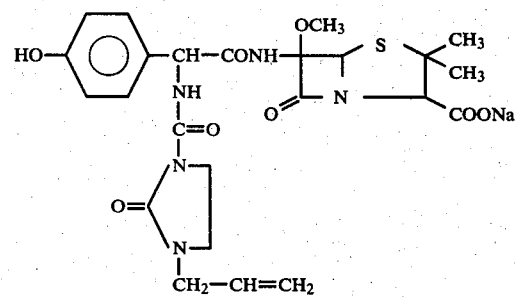

The procedure is as described in Example 1.

Yield 62% of 6-α-methoxy-6-β-{D-2-[3-(prop-2-enyl)-imidazolidin-2-on-1-yl-carbonylamino]-p-hydroxyphenylacetamido}-penicillanic acid (sodium salt)

Thin layer chromatogram: almost a single compound, about 90% pure; IR spectrum: 1,762 cm⁻¹.

The NMR spectrum is in agreement with the assumed structure.

EXAMPLE 14

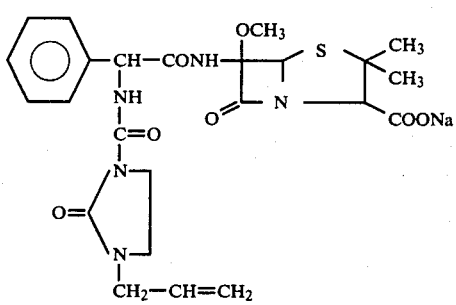

The procedure is as described in Example 1.

Yield 72% of 6β{D-2-[3-(prop-2-enyl)-imidazolidin-2-on-1-yl-carbonylamino]-phenylacetamido}-6-α-methoxypenicillanic acid (sodium salt)

Thin layer chromatogram: single compound; IR spectrum (Nujol): 1,765 cm$^{-1}$

NMR spectrum (CD$_3$OD): 0.9 s 3H, 1.15 s 3H, 3.4 m 2H (partially overlaid by the solvent) 3.5 s 3H, 3.9 m 2H+2H, 4.05 s 1H, 5.0–5.6 m 3H, 5.4 s 1H, 5.5 s 1H and 7.4 m 5H.

EXAMPLE 15

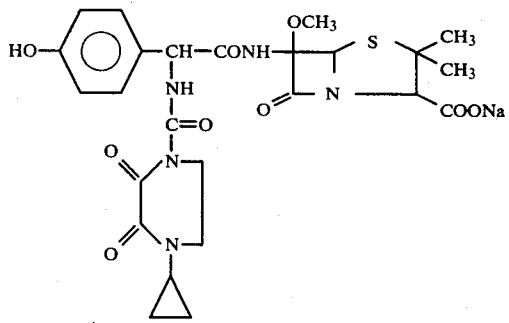

The procedure is as described in Example 1.

Compounds employed: 2.05 parts by weight of 6[D-α-(4-cyclopropyl-2,3-dioxo-1-piperazinocarbonylamino)-p-hydroxyphenyl-acetamido]-penicillanic acid, 0.18 part by weight of lithium hydride, 0.98 part by weight of t-butyl hypochlorite, 50 ml of absolute tetrahydrofuran and 50 ml of absolute CH$_3$OH.

Reaction time 3 hours at about −65° C.

Thin layer chromatogram: single compound; IR (Nujol): intense band at 1,760 cm$^{-1}$ NMR (CD$_3$OD): 0.75 d 4H, 1.05 s 3H, 1.4 s 3H, 2.8 p 1H, 3.3 m 4H, 3.45 s 3H, 4.05 s 1H, 5.4 s 1H, 5.5 s 1H, 6.75 m 2H and 7.3 m 2H.

Yield: 1.5 parts by weight (56%) of 6-α-methoxy-6-β-[D-2-(4-cyclopropyl-2,3-dioxo-1-piperazinocarbonylamino)-p-hydroxy-phenylacetamido]-penicillanic acid (sodium salt)

EXAMPLE 16

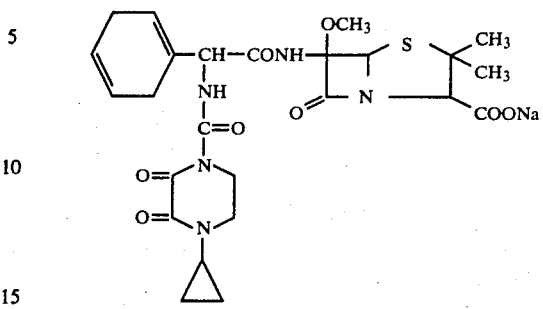

The procedure is as described in Example 1.

Yield: 58% of 6-α-methoxy-6β[D-2-(4-cyclopropyl-2,3-dioxo-1-piperazinocarbonylamino)-1,4-cyclohexadienylacetamido]-penicillanic acid (sodium salt)

Thin layer chromatogram: contains about 90% and small amounts of 2 impurities, IR spectrum: 1,760 cm$^{-1}$ NMR (CD$_3$OD): 0.7 d 4H, 0.9 s 3H, 1.15 s 3H, 3.65 broad 4H, 3.8 (partially overlaid) m 1H, 3.2 m 2H, 3.4 s 3H, 3.65 m 2H, 4.05 s 1H, 5.5 s 1H, 5.6 s 1H and 5.6–5.8 (partially overlaid) m 3H.

EXAMPLE 17

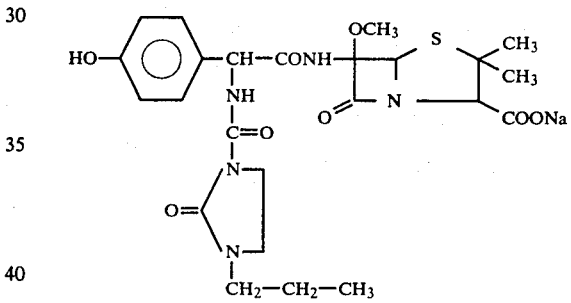

Yield: 64% of 6-α-methoxy-6-β-{D-2-[3-(propyl)imidazolidin-2-on-1-yl-carbonylamino]-p-hydroxyphenylacetamido}-pencillanic acid (sodium salt)

Thin layer chromatogram: single compound, IR spectrum: 1,765 cm$^{-1}$

EXAMPLE 18

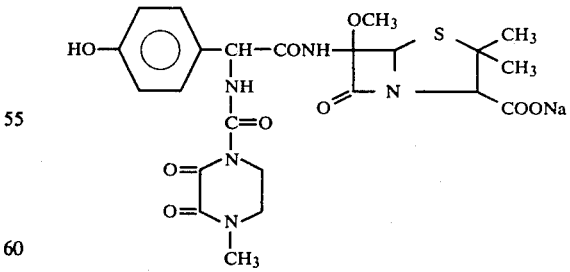

The procedure is as described in Example 1.

Yield: 64% of 6-α-methoxy-6-β-[D-2-(3-methylimidazolidin-2-on-1-yl-carbonylamino)-p-hydroxyphenylacetamido]-penicillanic acid (sodium salt)

Thin layer chromatogram: virtually uniform; IR spectrum: band at 1,765 cm$^{-1}$.

It will be appreciated that the instant specification and examples are set forth by way of illustration and not limitation, and that various modifications and changes may be made without departing from the spirit and scope of the present invention.

What we claim is:

1. A penicillin derivative of the formula

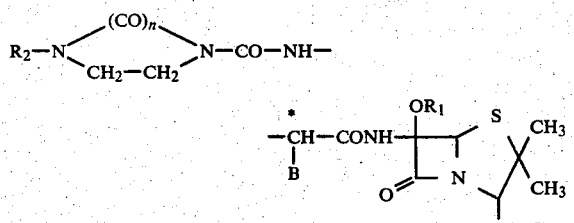

in which

R₁ is alkyl with 1 to 3 carbon atoms,

R₂ is hydrogen, alkyl with 1 to 4 carbon atoms, allyl, cyclopropyl, methylsulphonyl or phenylsulphonyl, B is phenyl, 4-hydroxyphenyl, cyclohexadienyl, and n is 1 or 2, or a pharmaceutically acceptable salt thereof.

2. A compound according to claim 1 of the formula

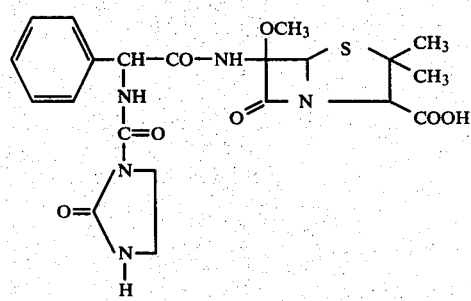

or a pharmaceutically acceptable salt thereof.

3. A compound according to claim 1 of the formula

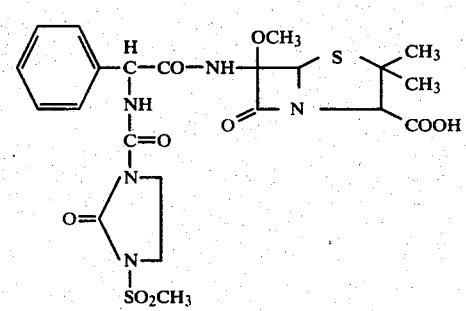

or a pharmaceutically acceptable salt thereof.

4. A compound according to claim 1 of the formula

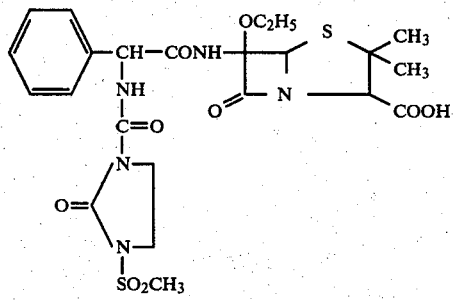

or a pharmaceutically acceptable salt thereof.

5. A compound according to claim 1 of the formula

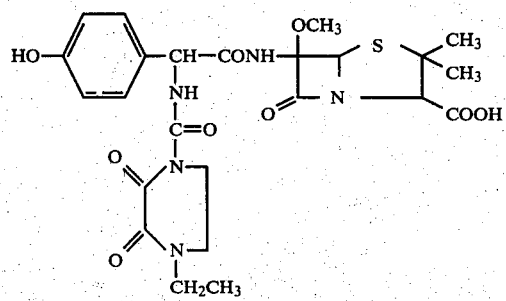

or a pharmaceutically acceptable salt thereof.

6. A compound according to claim 1 of the formula

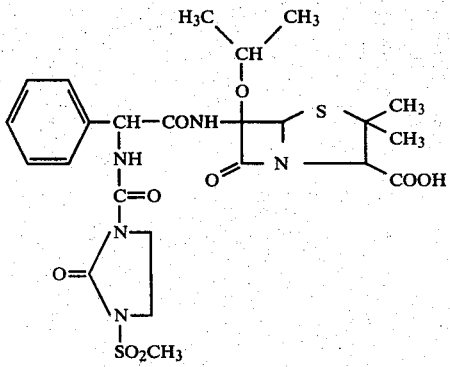

or a pharmaceutically acceptable salt thereof.

7. A compound according to claim 1 of the formula

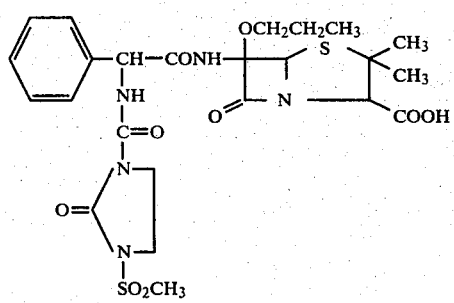

or a salt thereof.

8. A compound according to claim 1 of the formula

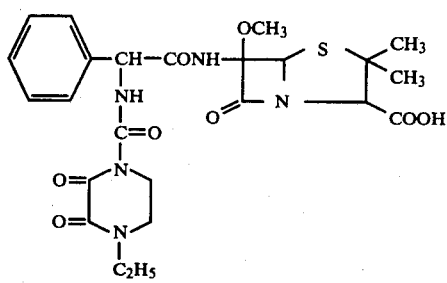

or a pharmaceutically acceptable salt thereof.

9. A compound according to claim 1 of the formula

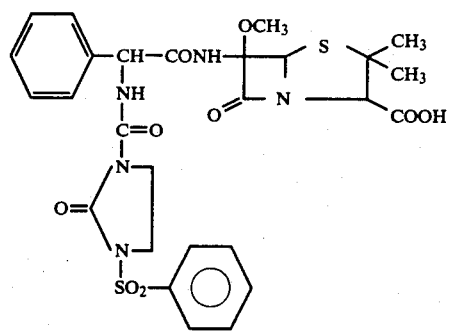

or a pharmaceutically acceptable salt thereof.

10. A compound according to claim 1 of the formula

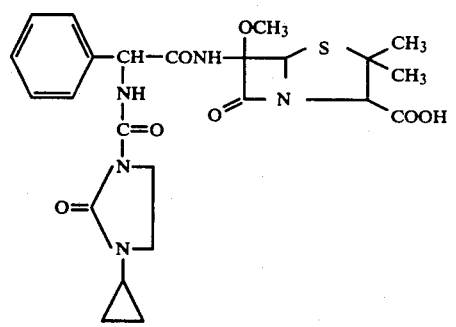

or a pharmaceutically acceptable salt thereof.

11. A compound according to claim 1 of the formula

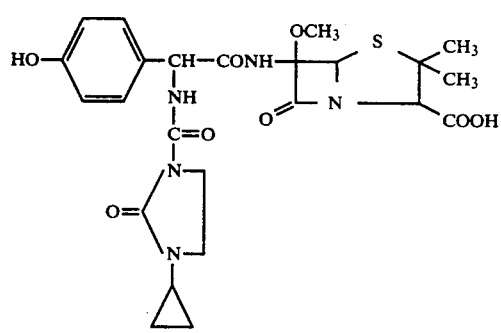

or a pharmaceutically acceptable salt thereof.

12. A compound according to claim 1 of the formula

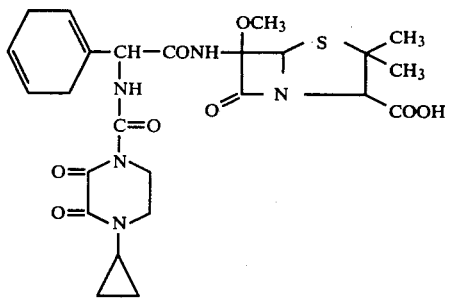

or a pharmaceutically acceptable salt thereof.

13. A compound according to claim 1 of the formula

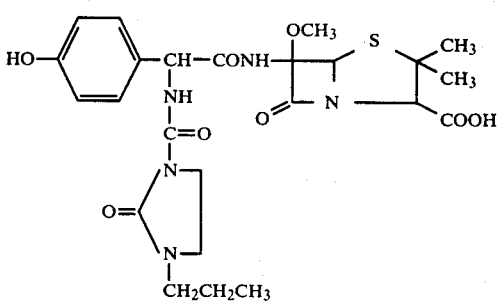

or a pharmaceutically acceptable salt thereof.

14. A compound according to claim 1 of the formula or a pharmaceutically acceptable salt thereof.

15. A compound according to claim 1 of the formula or a pharmaceutically acceptable salt thereof.

16. A compound according to claim 1 of the formula

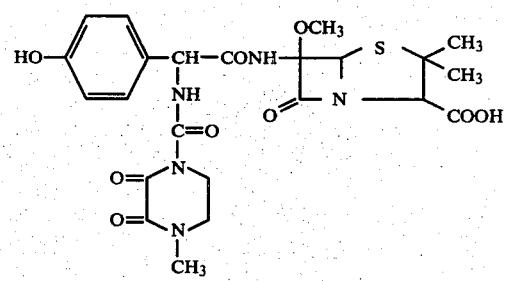

or a pharmaceutically acceptable salt thereof.

17. A compound according to claim 1 of the formula

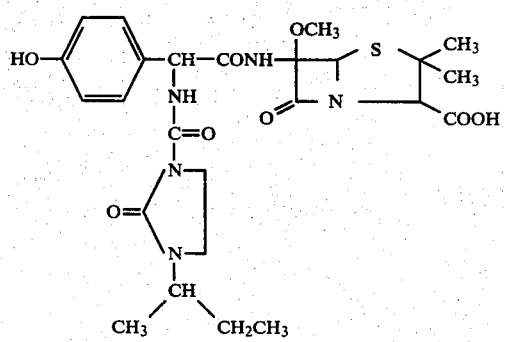

or a salt thereof.

18. A compound according to claim 1 of the formula

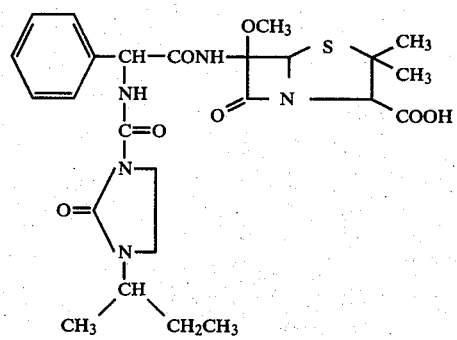

or a salt thereof.

19. A compound according to claim 1 of the formula

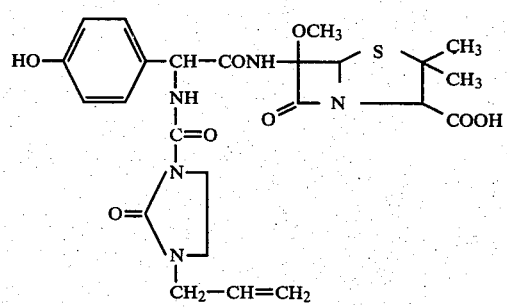

or a salt thereof.

20. An antibacterial composition containing as an active ingredient an antibacterially effective amount of a compound or pharmaceutically acceptable salt thereof according to claim 1 in admixture with a pharmaceutically acceptable diluent.

21. A medicament in dosage unit form comprising a composition according to claim 20.

22. A method of combating bacterial diseases in human and non-human animals which comprises administering to the animals an antibacterially effective amount of a compound or pharmaceutically acceptable salt thereof according to claim 1.

23. A method of promoting growth and improving feedstuff utilization in non-human animals which comprises administering to the animals a growth promoting amount of an active compound or pharmaceutically acceptable salt thereof according to claim 1.

24. An animal feedstuff comprising feed and a compound or a pharmaceutically acceptable salt thereof according to claim 1.

* * * * *

UNITED STATES PATENT AND TRADEMARK OFFICE
CERTIFICATE OF CORRECTION

PATENT NO. : 4,218,451

DATED : Aug. 19, 1980

INVENTOR(S) : Peter Feyen et al

It is certified that error appears in the above-identified patent and that said Letters Patent are hereby corrected as shown below:

Column 42, Line 66 insert -- pharmaceutically acceptable -- before "salt"

Signed and Sealed this

Twelfth Day of May 1981

[SEAL]

Attest:

RENE D. TEGTMEYER

Attesting Officer

Acting Commissioner of Patents and Trademarks